(12) United States Patent
Thauern et al.

(10) Patent No.: US 9,907,879 B2
(45) Date of Patent: Mar. 6, 2018

(54) HAEMOSTATIC COMPOSITION COMPRISING CRYSTALLINE POLYPHOSPHATE

(71) Applicant: BK Giulini GMBH, Ludwigshafen (DE)

(72) Inventors: Henrike Thauern, Weinheim (DE); Thomas Staffel, Grunstadt (DE)

(73) Assignee: BK GIULINI GMBH, Ludwigshafen (DE)

( * ) Notice: Subject to any disclaimer, the term of this patent is extended or adjusted under 35 U.S.C. 154(b) by 5 days.

(21) Appl. No.: 15/032,485

(22) PCT Filed: Oct. 30, 2014

(86) PCT No.: PCT/EP2014/073274
§ 371 (c)(1),
(2) Date: Apr. 27, 2016

(87) PCT Pub. No.: WO2015/063190
PCT Pub. Date: May 7, 2015

(65) Prior Publication Data
US 2016/0263275 A1    Sep. 15, 2016

(30) Foreign Application Priority Data
Oct. 31, 2013   (DE) .......................... 10 2013 222 223

(51) Int. Cl.
| | | |
|---|---|---|
| A61L 24/02 | (2006.01) | |
| A61L 15/18 | (2006.01) | |
| A61L 15/44 | (2006.01) | |
| A61L 26/00 | (2006.01) | |
| A61L 24/08 | (2006.01) | |
| A61L 24/10 | (2006.01) | |

(52) U.S. Cl.
CPC ............... *A61L 24/02* (2013.01); *A61L 15/18* (2013.01); *A61L 15/44* (2013.01); *A61L 24/08* (2013.01); *A61L 24/106* (2013.01); *A61L 24/108* (2013.01); *A61L 26/0004* (2013.01); *A61L 26/0066* (2013.01); *A61L 2300/112* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 2,852,341 A | 9/1958 | Bell et al. | |
| 3,658,579 A * | 4/1972 | Ottinger | ................... C08K 3/32 428/475.8 |
| 5,833,651 A * | 11/1998 | Donovan | ............... C12N 15/87 604/265 |
| 2004/0094279 A1 * | 5/2004 | Myatt | ..................... C09K 21/04 162/135 |
| 2006/0039994 A1 | 2/2006 | Davis | |
| 2006/0198837 A1 * | 9/2006 | Morrissey | ............... A61K 38/36 424/94.64 |
| 2007/0154510 A1 * | 7/2007 | Wilcher | ............ A61F 13/00034 424/422 |
| 2007/0160653 A1 | 7/2007 | Fischer et al. | |
| 2008/0145447 A1 | 6/2008 | Bedard | |
| 2009/0047366 A1 | 2/2009 | Bedard et al. | |

FOREIGN PATENT DOCUMENTS

WO    WO-2006096345 A3    9/2006

OTHER PUBLICATIONS

Smith et al., "Polyphosphate as a general procoagulant agent", Journal of Thrombosis and Haemostasis, vol. 6, (2008), pp. 1750-1756.

Smith et al.,"Polyphosphate modulates blood coagulation and fibrinolysis", PNAS, vol. 103, No. 104, (Jan. 24, 2006), pp. 903-908.

Smith et al., "Polyphospahte enhance fibrin clot structure", Hemostasis, Thrombosis, and Vascular Biology, vol. 112, (Oct. 2008), No. 7, pp. 2810-2816.

Muller et al., "Platelet Polyphosphates Are Proinflammatory and Procoagulant Mediators In Vivo", Cell vol. 139, (Dec. 11, 2009), pp. 1143-1156.

Smith et al., "Polyphosphate exerts differential effects on blood clotting, depending on polymer size", Thrombosis and Hemostasis, vol. 116, (Nov. 2010), pp. 4353-4359.

Ullmann's Encyclopedia of Industrial Chemistry, vol. 26, pp. 676-724 (specifically pp. 694-711).

Hemker et al., "Thrombin generation, a function test of the haemostatic-thrombotic system", 2006 Schattauer GmbH, Stuttgart, pp. 553-561.

* cited by examiner

*Primary Examiner* — Robert A Wax
*Assistant Examiner* — Quanglong N Truong
(74) *Attorney, Agent, or Firm* — Venable LLP; Keith G. Haddaway; Annette K. Kwok (57) ABSTRACT

The present invention relates to the use of polyphosphate in crystalline form for treatment of wounds, especially bleeding wounds, wherein the anion of the polyphosphate has a (numerical) average of at least 4 phosphorus atoms per polyphosphate anion. The invention additionally relates to a composition suitable for treatment of wounds, especially bleeding wounds, comprising an inventive polyphosphate and a carrier material. The invention further provides a method suitable for production of the inventive composition, which comprises the introduction of the polyphosphate and optionally further haemostatic agents into the carrier material, or into a component or into a precursor of the carrier material.

14 Claims, 4 Drawing Sheets

HAEMOSTATIC COMPOSITION COMPRISING CRYSTALLINE POLYPHOSPHATE

CROSS-REFERENCE TO RELATED APPLICATIONS

This application is a 371 National Stage of International Application No. PCT/EP2014/073274, filed Oct. 30, 2014, which claims priority to German Application No 10 2013 222 223.8, filed Oct. 31, 2013, each of which is hereby incorporated by reference in their its entirety.

The present invention relates to uses of crystalline polyphosphate for treating bleeding wounds, to compositions containing crystalline polyphosphate and to methods for preparing such compositions.

Injuries to human and animal tissue layers may damage blood vessels situated therein, and this can lead to escape of blood at the affected site on the skin or in the body interior. After a phase of escape of blood, the natural blood coagulation process starts. Blood coagulation refers to the solidification of the liquid blood as a physiological protection mechanism. Blood coagulation is based on two enzymatic reaction pathways which are complex and proceed in the manner of a cascade and in which multiple coagulation factors play a part. Both pathways, which are typically referred to as the intrinsic pathway and the extrinsic pathway, lead to the formation of insoluble fibrin strands, which are substantially involved in the accomplishment of wound-closing blood clots. Thrombin, also called coagulation factor IIa, occupies a key role here, since it not only brings about the formation of fibrin, but also intervenes in an activating manner at multiple points in the coagulation cascade by means of positive feedback.

Although the natural blood coagulation process starts almost immediately after onset of the trauma, it is a relatively slow process which takes up some time for closure of the wound and associated hemostasis. In many cases, a quickened hemostasis is therefore desirable, for example in the interests of hygiene or when there are concerns about an excessive loss of blood owing to the size of the wound or the severity of the blood flow. Well-known techniques for hemostasis, such as, for instance, covering the wound, applying compression bandages and stapling or stitching the wound, are frequently insufficient. Therefore, methods intended to contribute to improving hemostasis are known from the prior art, for example the introduction of blood coagulation-active substances such as fibrin glue into the wound region. More recently, uses of inorganic substances as hemostatic agents have been described, for example in the following patent documents:

US 2007/0160653 relates to textiles which contain glass fibers and which activate endogenous hemostasis.

The techniques described in US 2006/0039994 for promoting blood coagulation are based on the action of molecular sieves based on aluminophosphate.

US 2008/0145447 and US 2009/0047366 describe diatomaceous earth, silica gel, glass fibers, quartz sand, calcium silicate and amorphous calcium polyphosphate as blood coagulation-stimulating substances.

The activating influences of water-soluble polyphosphates on blood coagulation are discussed by S. A. Smith et al., PNAS 2006, 103(4), 903-908; S. A. Smith et al., J. Thromb. Haemost. 2008, 6(10), 1750-1756; S. A. Smith et al., Blood 2008, 112, 2810-2816; F. Müller et al., Cell 2009, 139, 1143-1156; and S. A. Smith et al., Blood 2010, 116, 4353-4359. Furthermore, EP 1 869 082 describes the use of water-soluble polyphosphate having a chain length of at least 25 for staunching or slowing wound bleeding.

The particulate substances for hemostasis that are known from the prior art are, in the majority of cases, nonphysiological substances, the tolerability of which for the human or animal organism upon contact with wound tissue is frequently questionable and which are possibly allergy-triggering. Moreover, there is no guarantee for many of said particulate substances that they are free of potentially toxic or otherwise intolerable contaminants. The completely water-soluble polyphosphate used, for example, in EP 1869 082 is associated with disadvantages too. For instance, in the case of severe bleeding, it is rapidly washed away from the wound area and thus becomes ineffective, whereas in the case of relatively weak bleeding, it can easily reach the bloodstream and can have undesired effects on sites of the body that are far removed from the wound, such as the formation of thrombotic blood clots for example.

It is therefore an object of the invention to provide a physiologically tolerable hemostatic substance and a corresponding composition for wound treatment, which overcome the problems of the products of the prior art, can be prepared in a simple and cost-effective manner, and are easily and reliably applicable in medical practice by means of conventional techniques.

It was found that, surprisingly, the stated object is achieved by the treatment of wounds with polyphosphate in crystalline form, the anion of the polyphosphate having on average (number average) at least 4 phosphorus atoms per polyphosphate anion.

Said crystalline polyphosphates not only have a very good hemostatic action, but are also easy to handle, physiologically tolerable, and can be prepared cost-effectively in highly pure form.

Therefore, the invention provides for the use of polyphosphate in crystalline form for treating wounds, more particularly bleeding wounds, wherein the anion of the polyphosphate has on average (number average) at least 4 phosphorus atoms per polyphosphate anion.

The invention further provides compositions comprising a crystalline-form polyphosphate according to the invention and a carrier material. Said compositions are suitable for treating wounds, more particularly bleeding wounds.

The invention further provides methods for preparing the composition according to the invention, comprising introducing the polyphosphate and optionally further hemostatic agents into the carrier material, or into a component or into a precursor of the carrier material.

The crystalline polyphosphates according to the invention generally have a degree of crystallinity of at least 90%, preferably at least 95% and more particularly at least 98%. The degree of crystallinity of the polyphosphate can be determined in a manner known per se by means of X-ray powder diffractometry or by DSC measurements.

The anions of the crystalline polyphosphates of the invention are generally substantially linear, i.e., to an extent of at least 80 mol %, preferably at least 90 mol % and more particularly at least 95 mol %, based on the polyphosphate.

The cations of the crystalline polyphosphates are preferably alkali metal, alkaline earth metal, metal or ammonium ions independently selected especially from $Na^+$, $K^+$, $NH_4^+$, $Ca^{2+}$, $Mg^{2+}$, $Zn^{2+}$, $Sn^{2+}$, $Fe^{3+}$ and $Al^{3+}$, preferably from $Na^+$, $K^+$, $NH_4^+$ and $Ca^{2+}$.

In a preferred embodiment of the invention, the polyphosphate anions of the polyphosphates according to the invention have on average (number average) from 8 to 500, preferably from 12 to 300 and more particularly from 15 to 150 phosphorus atoms per polyphosphate anion. The number-average number of phosphorus atoms in the polyphosphate anion can be determined in a manner known per se, for example by $^{31}$P solid-state NMR, for example by means of the approach described in more detail below.

In the context of the present invention, "linear polyphosphates" are the salts of noncyclic polyphosphate anions. Thus, the linear polyphosphates of the invention are chains of metaphosphate units $PO_3^-$, in which two phosphorus atoms at a time are connected to one another via an oxygen atom. Accordingly, "chain length" is understood here to mean the number of the metaphosphate units $PO_3^-$ present in the polyphosphate anion. The linear crystalline polyphosphates of the invention can be described by the formula A:

(A)

In the formula A, n represents on average (number average) a number from 4 to 1000, preferably from 8 to 500, more particularly from 12 to 300 and specifically from 15 to 150. M represents a cation or a cation equivalent independently selected in each case preferably from $Na^+$, $K^+$, $\tfrac{1}{2}Ca^{2+}$ and $NH_4^+$. Thus, the variable n in the formula A corresponds to the number-average chain length of the linear polyphosphate or to the number-average number of the phosphorus atoms in the polyphosphate anion. The expression "$\tfrac{1}{2}Ca^{2+}$" makes it clear here that, owing to the double positive charge thereof, each $Ca^{2+}$ present in the polyphosphate of the formula A represents two cations M in the formula A.

The crystalline polyphosphates used according to the invention are notable for high purities. For instance, the proportion of water which may still be present as residual moisture in the crystalline polyphosphate is typically less than 1% by weight, preferably less than 0.5% by weight and more particularly less than 0.3% by weight, based on the total weight of the polyphosphate. The proportion of ingredients in which the ingredient is not phosphates or water is generally less than 0.1% by weight, preferably less than 0.05% by weight and more particularly less than 0.01% by weight, with regard to the total weight of the polyphosphate. In this connection, phosphates are understood to mean mono-, meta-, pyro-, tri- and polyphosphates. Furthermore, the proportion of mono-, meta-, pyro- and triphosphates and also polyphosphates, the chain length of which deviates at least 20% from the number-average chain length of the particular polyphosphate according to the invention, is generally less than 10% by weight, preferably less than 7.5% by weight and more particularly less than 5% by weight, with regard to the total weight of the polyphosphate.

Furthermore, the crystalline polyphosphates used according to the invention are notable for the fact that they are substantially water-insoluble. For instance, their proportion of water-soluble constituents is generally less than 8% by weight, preferably less than 5% by weight and more particularly less than 3% by weight, with regard to the total weight of the polyphosphate. Here, water-soluble refers to those constituents which, in the form of a powder, dissolve in water at 25° C. at a rate of at least 50% by weight per hour. Such water-soluble constituents are practically exclusively the aforementioned mono-, meta-, pyro- and triphosphates, which have a high solubility in water.

In a preferred embodiment of the invention, all cations of the polyphosphate according to the invention are selected from $Na^+$, $K^+$, $Ca^{2+}$ and $NH_4^+$ and more particularly from $Na^+$, $K^+$ and $NH_4^+$. Particularly preferably, all cations of the polyphosphate are either $Na^+$, $K^+$, $Ca^{2+}$ or $NH_4^+$ and more particularly $Na^+$, $K^+$ or $NH_4^+$, i.e., the polyphosphate does not contain different cations.

The crystalline-form polyphosphates according to the present invention can be prepared by means of methods which are known from the prior art and which are, for example, described by K. Schrödter et al. in: Ullmann's Encyclopedia of Industrial Chemistry, "Phosphoric Acid and Phosphates", pages 32-41, 2008 (7th edition), New York, N.Y., Wiley-VCH Verlag. For instance, crystalline sodium polyphosphates such as Kurrol's salt and Maddrell's salt can, for example, be prepared by annealing amorphous, glassy sodium polyphosphate, which on its part can be prepared by heating sodium dihydrogen phosphate and sodium hydrogen phosphate with release of the water of condensation and then quenching the melt obtained. Crystalline potassium and calcium polyphosphates can be prepared in a similar manner, for example by heating $KH_2PO_4$ or $Ca(H_2PO_4)_2$. By contrast, crystalline ammonium polyphosphates can, for example, be prepared by reacting phosphoric acid with ammonia-releasing compounds, such as urea, melamine or methenamine for instance, or alternatively reacting phosphorus pentoxide with diammonium phosphate in ammonia.

In a particularly preferred embodiment of the invention, the crystalline-form polyphosphates are selected from linear sodium polyphosphates, i.e., polyphosphates of the formula A where each M represents $Na^+$, having a number-average chain length of from 15 to 100, preferably from 20 to 80, more particularly from 30 to 60 and specifically from 35 to 55, linear ammonium polyphosphates, i.e., polyphosphates of the formula A where each M represents $NH_4^+$, having a number-average chain length of from 12 to 200, preferably from 17 to 150, more particularly from 20 to 135 and specifically from 22 to 125, linear calcium polyphosphates, i.e., polyphosphates of the formula A where each M represents $\tfrac{1}{2}Ca^{2+}$, having a number-average chain length of from 8 to 100, preferably from 10 to 60, more particularly from 10 to 40 and specifically from 12 to 25, and linear potassium polyphosphates, i.e., polyphosphates of the formula A where each M represents $K^+$, having a number-average chain length of from 12 to 100, preferably from 18 to 70, more particularly from 22 to 50 and specifically from 25 to 40.

The crystalline polyphosphates of the invention are typically used in particulate form in the uses according to the invention for hemostasis and in the compositions according to the invention for wound treatment. This is understood here to mean that the polyphosphate consists of particles to an extent of at least 90% by weight, which particles generally have a diameter of no greater than 5 mm and more particularly no greater than 2 mm. The weight-average particle size of the polyphosphate used for the purposes of hemostasis is generally within the range of 0.1 μm to 5 mm, preferably 0.5 μm to 2 mm, more particularly 1 μm to 1 mm and specifically 5 μm to 0.5 mm. The particle sizes specified here and hereinbelow can be determined in a manner known per se by means of sieve analysis or by light scattering. Corresponding particulate polyphosphates with a suitable particle size distribution can be obtained by means of comminution of the crystalline polyphosphates according to the invention in a manner known per se, more particularly by grinding, for example by means of a ball mill.

In the uses according to the invention for treating bleeding wounds, the crystalline polyphosphates of the invention, preferably present in particulate form, are contacted with the blood escaping from the wound. As a result of the contact with the blood, the crystalline polyphosphate activates one or more endogenous processes, which result in a hemostatic action, i.e., reduce, slow or stop the blood flow. These processes activated by the crystalline polyphosphate are presumably primarily those which are influenced and especially activated by thrombin. These are probably predominantly processes which bring about blood coagulation by formation of insoluble fibrin. For instance, it is, for example, conceivable that the contact activation of the coagulation cascade, as is known for the intrinsic system, is triggered by the crystalline polyphosphate according to the invention.

It has been found that the contact of the crystalline polyphosphate with blood in the uses according to the invention leads to an increase in the thrombin content in the blood. In particular, this is an exponential rise in the thrombin content.

The use according to the invention of crystalline polyphosphates for hemostasis can be effected such that the polyphosphate preferably present in particulate form is used as such. In this connection, it is, for example, possible to introduce particulate polyphosphate into the bleeding wound or to partly or completely cover the wound with particulate polyphosphate, ensuring a very intensive contact between polyphosphate and blood. Thereafter, the wound treated in this manner can be covered or closed by means of known materials, such as bandaging materials in particular, in order to protect the wound and to fix the polyphosphate particles.

Preferably, the use according to the invention of crystalline polyphosphates for hemostasis is, however, effected such that the wound is treated with a composition according to the invention comprising the crystalline polyphosphate and a carrier material. In this connection, the carrier material serves especially to retain or to fix the preferably particulate polyphosphate such that a penetration of the polyphosphate into deeper wound regions is prevented, though ensuring at the same time an intensive contact of the polyphosphate particles with the escaping blood.

The carrier materials present in the compositions according to the invention are preferably selected from textile materials, liquids, gels, powders and combinations thereof, these materials being especially those which are known to be suitable for the treatment of wounds and which are already used for this purpose.

Especially suitable textile carrier materials are planar wovens and nonwovens. The wovens and nonwovens are, for example, made from natural fibers, for example cotton, synthetic fibers, for example polyester or polyamide fibers, or mixtures of fibers. Said planar textiles can be used in the compositions according to the invention in single-layer or multilayer form, it being possible for layers composed of woven to be also used in combination with those composed of nonwoven. Examples of suitable planar textiles are gauze, lint and other planar wound dressings which contain fibers. Furthermore, it is also possible to use nonplanar textile materials, such as wadding, fiber bundles and swabs for example, as carrier material. Compositions for wound treatment that are based on such textile carrier materials are, for example, wound dressings, bandaging materials, dressings, compresses, bandages and plasters.

Suitable liquid carrier materials are especially hydrophilic, more particularly aqueous, liquids and hydrophobic, more particularly oil-containing or fat-containing, liquids, and also mixtures thereof. Said liquids can contain further substances, such as, for example, salts, particulate active ingredients or gases, in dissolved or undissolved form. Suitable mixtures of hydrophilic and hydrophobic liquids are especially oil-in-water and water-in-oil emulsions, which may optionally contain emulsifying substances and further ingredients. Examples of such liquids are water, aqueous solutions, lotions, creams and ointments. Compositions for wound treatment that are based on such liquids are, for example, wound creams, wound pastes, wound emulsions, wound sprays in which the liquid is transferred to an aerosol by a propellant, and wound foams.

Gels suitable as carrier material are especially hydrogels with a solid phase which is based on natural or synthetic polymers. Examples of such polymers are polyvinyl alcohols, acrylate-based polymers and copolymers, thickening-acting polysaccharides such as agarose, methylcellulose, hyaluronic acid, and also derivatives and mixtures of these polymers. The aqueous phase of said gels can contain further components in dissolved form. Compositions for wound treatment that are based on such gels are especially wound gels.

Suitable pulverulent carrier materials are, for example, fine-particle minerals, such as zeolites, silica gel, diatomaceous earth or kaolin, and fine-particle polysaccharides, such as cellulose or cellulose derivatives, and also mixtures of these materials. These powders can contain further solid substances bound to the powder particles by noncovalent bonding. Compositions for wound treatment that are based on such powders include especially wound powders.

Accordingly, compositions according to the invention that are preferred are those present in the form of a wound dressing, a bandaging material, a wound powder, a wound spray, a wound foam, a wound gel, a wound cream or a wound paste.

Furthermore, compositions according to the invention that are preferred are those in which the crystalline polyphosphate is present distributed in particulate form in the carrier material of said compositions, it being possible for the polyphosphate particles to be distributed in the entire carrier material or in only a portion thereof. Preferably, the polyphosphate particles are evenly or approximately evenly distributed in the carrier material or a portion thereof, i.e., the carrier material or the portion thereof in which the particles are situated could be divided into equally sized or approximately equally sized segments in which only one particle is situated in each case.

In one embodiment of the invention, the crystalline polyphosphate is present distributed in particulate form in one or more approximately two-dimensional layers of the carrier material. For example, the polyphosphate particles can be enclosed between two layers of a planar, blood-permeable carrier material, more particularly a woven or a nonwoven.

In a further embodiment of the invention, the crystalline polyphosphate is present distributed in particulate form in a three-dimensional carrier material or a three-dimensional region of the carrier material. For example, the polyphosphate particles can be distributed within the volume of a fiber bundle, cotton wad or gel.

According to one embodiment of the invention, the composition according to the invention can additionally contain at least one further hemostatic agent, which is preferably a substance, the hemostatic action of which is known from the prior art. Preferably, said additional hemostatic agent is selected from chitosan, the derivatives thereof, thrombin, fibrin, fibrinogen and $Ca^{2+}$-ion-containing substances different from crystalline calcium polyphosphate, such as calcium chloride for example.

The compositions according to the invention can contain further components which have been found to be helpful in compositions for wound treatment, such as, for example, adhesive elements for fastening on the skin or an outer coat which protects the wound from external influences or minimizes the escape of blood.

In a preferred embodiment of the invention, the composition according to the invention for wound treatment is used in sterile form. Accordingly, the invention also provides compositions according to the invention that are sterile and also compositions according to the invention in sterile form that are enclosed in an item of packaging, and so they do not lose their sterility even over relatively long storage periods.

Preferred methods for preparing the compositions according to the invention for the treatment of bleeding wounds comprise one or more steps suited to incorporating the particulate-form crystalline polyphosphate, and optionally one or more further hemostatic agents, into the carrier material, into a component of the carrier material or into a precursor of the carrier material. In this connection, "component of the carrier material" represents a particular part of the carrier material, such as, for example, a layer of woven within a multilayer textile carrier material, or the liquid phase of a gel consisting of a solid and a liquid phase. "Precursor of the carrier material" represents here a substance from which the carrier material or a portion thereof can be produced by chemical conversion, such as, for example, a monomer used to prepare a polymeric carrier material.

The incorporation of the crystalline polyphosphate into the carrier material, a component thereof or a precursor thereof is generally achieved by contacting the carrier material, the component or the precursor with the polyphosphate. If the carrier material, the component or the precursor is present in liquid or particulate form, the incorporation is preferably carried out by mixing with the polyphosphate particles. In this way, it is possible to incorporate polyphosphate particles especially into the carrier materials powders and liquids, it being possible for the latter to also be carrier material components, for example of an emulsion or of a gel. In the case of a liquid or dissolved monomer as carrier material precursor, the polyphosphate particles can be mixed with the monomer and the polymeric carrier material comprising the particles can then be obtained therefrom by polymerization.

If the carrier material, the component thereof or the precursor thereof is a textile material or another solid, nonparticulate material permeable to gases or liquids, the incorporation can, for example, be achieved by blowing the polyphosphate particles into the material, for instance by means of an air stream, or by treating the material with a suspension containing the particles. For example, by immersing a nonwoven into an agitated aqueous suspension of the particles, subsequently removing the aqueous phase and drying the nonwoven, it is possible to obtain a nonwoven which is loaded largely uniformly with polyphosphate particles and which is suitable as composition according to the invention for wound treatment.

To treat a bleeding wound, the composition according to the invention in the wound region is generally applied in the wound region such that the wound or the wound region is covered by the composition at least partly, preferably completely or for the most part. After application, the carrier material is preferably situated in the immediate vicinity of or in contact with the wound tissue. Therefore, according to a preferred embodiment, the carrier material is capable of adjusting to the shape of the wound to a certain extent or already has, prior to application, approximately the shape of the wound. Therefore, a person skilled in the art is, without any problems, capable of selecting for a multiplicity of very different wounds the best particular composition according to the invention for hemostatic treatment, by identifying for the particular wound a suitable carrier material or a suitable combination of carrier materials.

The crystalline polyphosphates according to the invention and compositions for wound treatment that contain such polyphosphates are notable for excellent hemostatic action. Moreover, they can be prepared in a cost-effective manner, are easy to handle, are suitable for the treatment of a very wide variety of different bleeding wounds and are physiologically well-tolerated.

The figures and examples which follow provide more particular elucidation of the uses and compositions according to the invention.

FIGURES

FIGS. 1 to 4 show graphs depicting the thrombin concentrations in blood plasma, as determined by the herein-described assay for real-time measurement of thrombin formation, after addition of polyphosphate in relation to time (so-called thrombograms). The abbreviation "w/o" means in each case that no polyphosphate was added. The thrombograms measured without polyphosphate (i.e., the w/o lines) are in each case on the x-axis of the graph.

EXAMPLES

Determination of Solubility:

The polyphosphates to be investigated were each weighed out in a 250 ml Erlenmeyer flask (5 g±0.01 g) and admixed with distilled water (50 ml, 20-22° C.). The mixture thus obtained was shaken at 200 revolutions per minute (rpm, rotary movement) for 20 min. Thereafter, the mixture was transferred to a centrifuge tube and centrifuged at 5000 rpm for 20 min. 10 ml of the supernatant solution were pipetted into a predried aluminum bowl (diameter of 60 mm, height of 15 mm), which was then dried at 105° C. in a forced-air oven for 150 min. The solubility in g per 100 g of water was then obtained from the formula TR×10, where TR represents the determined dry residue in grams.

Determination of the Chain Length of Polyphosphates:

For the polyphosphates used, a $^{31}P$ solid-state NMR spectrum was recorded and the integrals of the signals of the centrally located phosphate groups (a) as well as the integrals of the signals of the terminal phosphate groups (b) were determined. The number-average chain length K could then be determined in each case with the aid of the formula $K=2(a/b+1)$. For some of the water-soluble polyphosphates serving as comparison, the number-average chain length K was accordingly also determined in solution ($D_2O$) by means of $^{31}$P NMR. The values obtained for the chain lengths K of the investigated polyphosphates are listed in Table 1.

Determination of the Degree of Crystallinity of Polyphosphates

The degrees of crystallinity of the investigated polyphosphates were determined on the basis of their X-ray powder diffractograms. This involved using the full widths at half maximum of the recorded signals of the diffractograms in a manner known per se to quantify the crystallinity.

The following polyphosphates were used:
(1) sodium triphosphate: sodium tripolyphosphate 1331 (BK Giulini);
(2) sodium oligophosphate: sodium polyphosphate P60 (BK Giulini);
(3) sodium polyphosphate A: sodium polyphosphate P64 (BK Giulini);
(4) sodium polyphosphate B: sodium polyphosphate P68 hexametaphosphate (BK Giulini);
(5) sodium polyphosphate C: sodium polyphosphate P70 (BK Giulini);
(6) sodium polyphosphate D: acidic sodium polyphosphate P70.5 (BK Giulini);
(7) sodium polyphosphate E: Maddrell's salt (BK Giulini);
(8) ammonium polyphosphate A: Phos-Chek P30 (BK Giulini);
(9) ammonium polyphosphate B: Phos-Chek P42 (BK Giulini);
(10) calcium polyphosphate: laboratory product from BK Giulini;
(11) potassium polyphosphate: potassium metaphosphate (BK Giulini);
(12) sodium trimetaphosphate: sodium trimetaphosphate (BK Giulini);
(13) calcium hydrogen phosphate: DCP-D, dicalcium phosphate dihydrate (BK Giulini);

Assay for Measuring Thrombin Formation in Real-Time

Figure 1:
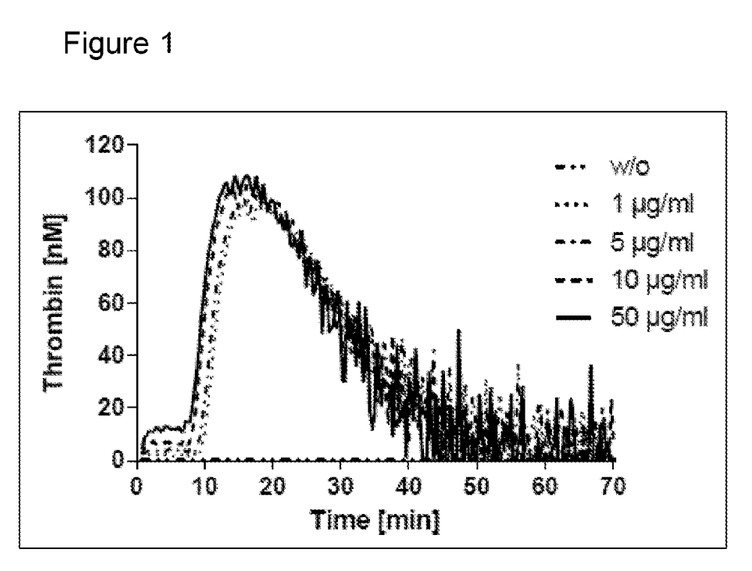
FIG. 1: Thrombogram determined in the presence of 0, 1, 5, 10 and 50 µg/ml crystalline ammonium polyphosphate 1 (chain length K: 38).
Figure 2:
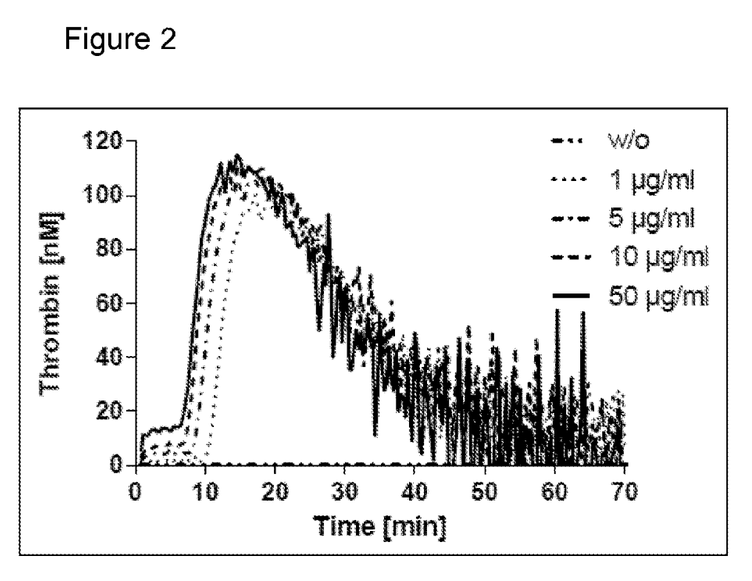
FIG. 2: Thrombogram determined in the presence of 0, 1, 5, 10 and 50 µg/ml crystalline potassium polyphosphate (chain length K: 31).
Figure 3:
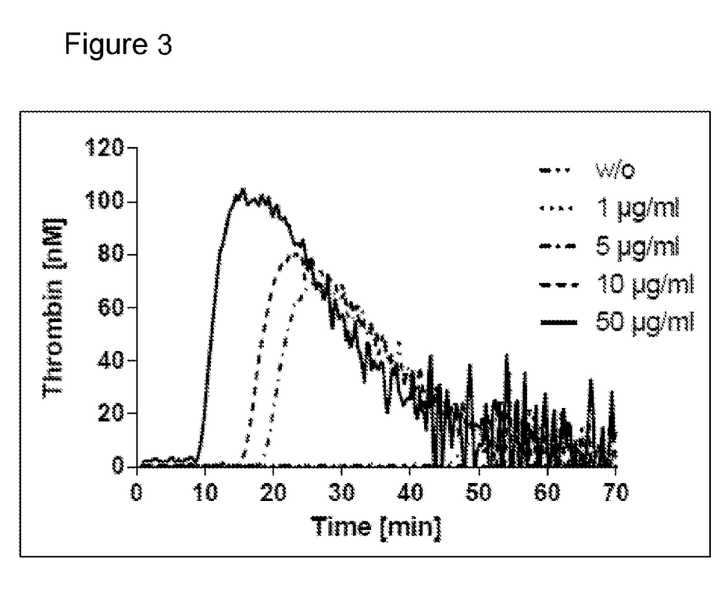
FIG. 3: Thrombogram determined in the presence of 0, 1, 5, 10 and 50 µg/ml crystalline sodium polyphosphate (chain length K: 44).
Figure 4:
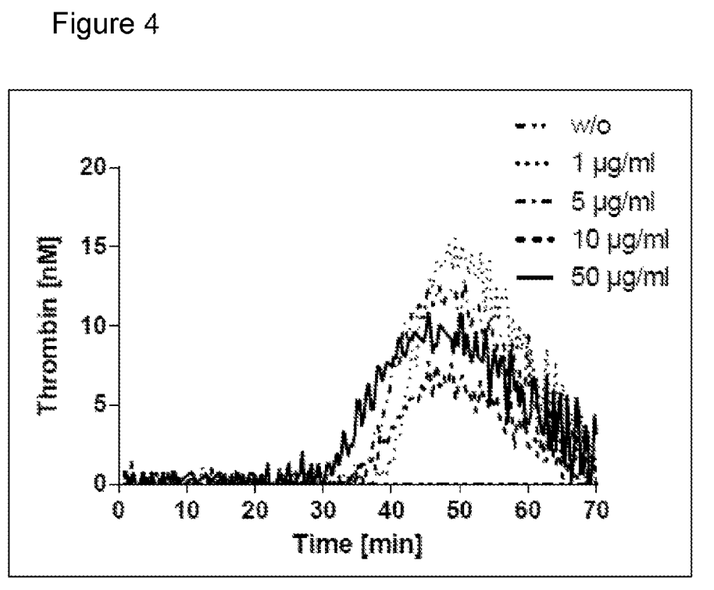
FIG. 4: Thrombogram determined in the presence of 0, 1, 5, 10 and 50 µg/ml amorphous, water-soluble sodium polyphosphate 3 (chain length K: approx. 27).

This method was used to determine the formation of thrombin in blood plasma, triggered in each case by the polyphosphates, in relation to time and to the amounts of polyphosphate used. With the aid of the so-called thrombograms thus obtained, it is possible to draw conclusions concerning the response rate and the extent of thrombin formation. The measurements were carried out in accordance with the instructions from Thrombinoscope BV (manufacturer of the below-mentioned fluorogenic substrate) in a fluorometer (Fluoroscan Ascent, Thermo Scientific) equipped with a dispenser (see F. Müller et al., Cell 2009, 139, 1143-1156 and Supplemental Data). In said measurements, the thrombin formation occurred in a total volume of 120 µl which contained low-thrombocyte plasma (80 µl), tissue factor (0.5 pM or 0.0 pM), factor VIIa inhibited at the active site, phospholipid (4 µM) consisting of phosphatidylserine, phosphatidylethanolamine and phosphatidylcholine in the ratio of 20 mol %/20 mol %/60 mol %, $Ca^{2+}$ (20 mM) and the fluorogenic substrate Z-Gly-Gly-Arg-7-amino-4-methylcoumarin (2.5 mM, ZGGR-AMC, Thrombinoscope BV). Trypsin inhibitor from maize, monoclonal antibodies against human "tissue factor pathway inhibitor" (TFPI) or "thrombin activatable fibrinolysis inhibitor" (TAFI) and carboxypeptidase inhibitor (all from Sigma-Aldrich GmbH) were added up to final concentrations of 40 µg/ml, 1 µg/ml or 10 µg/ml. Inner filter effects and the substrate consumption were corrected by calibrating each measurement against a fluorescence curve which was determined by means of a mixture of the plasma (80 µl) with a fixed amount of thrombin/α2-macroglobulin complex (Thrombin Calibrator, Thrombinoscope BV). All measurements were each left to run for 60 min and carried out in duplicate. The values obtained relating to thrombin formation were calibrated using the software from Thrombinoscope (version 3.0.0.29). The data determined for ammonium polyphosphate 1 (chain length K: 38), potassium polyphosphate (chain length K: 31), sodium polyphosphate (chain length K: 44) and water-soluble sodium polyphosphate 3 (chain length K: approx. 27) as comparative example are summarized in the thrombograms in FIGS. 1 to 4.

Characteristic of the thrombograms are, in particular, the delay time and the endogenous thrombin potential (ETP). The delay time is the period of time from time 0 up to the start of the explosive rise in thrombin concentration. ETP refers to the integral of the measured curve of the thrombin concentration. The delay time corresponds in a first approximation to the time until onset of blood coagulation, whereas the ETP is a good indicator of the extent of blood coagulation (cf. Hemker et al., Thromb. Haemost. 2006, 96 (55), 553-561).

The comparison of the thrombograms for the crystalline polyphosphates according to the invention with the thrombogram of the water-soluble sodium polyphosphate 3 shows that the polyphosphates according to the invention have a lag time that is about 3 to 5 times shorter and additionally have ETPs that are many times larger. It can be concluded therefrom that, with respect to the water-soluble sodium polyphosphate 3, the water-insoluble, crystalline polyphosphates of the invention not only result in a drastically shortened period of time until the onset of blood coagulation, but also lead to an enormous rise in thrombin concentration and thus to a very much more intense blood coagulation.

Table 1 below characterizes the investigated phosphates in terms of their water solubility, their chain length, their solid structure and their hemostatic action. Here, water-soluble refers to phosphates having a water solubility of at least 1 g per 100 g of water, as determined by the above-described technique. Here, hemostatic refers to phosphates where the thrombograms, as determined by the above-described technique, have a maximum thrombin concentration of at least 50 nM. As can be clearly read off from Table 1, all the crystalline, water-insoluble polyphosphates according to the invention are notable for a hemostatic action, whereas amorphous, water-soluble polyphosphates and also crystalline mono-, tri- and metaphosphates are not hemostatic.

TABLE 1

Hemostatic action of the polyphosphates according to the invention as per Examples 1 to 5 and of the phosphates or polyphosphates not in accordance with the invention as per Examples V1 to V8.

| Example | Phosphates investigated | Structure | Chain length K as per $^{31}$P NMR in: solid phase | solution | Water-soluble | Hemostatic |
|---|---|---|---|---|---|---|
| V1 | Sodium triphosphate | Crystalline | 3 | 3 | Yes | No |
| V2 | Sodium oligo-phosphate | Amorphous | — | 5 | Yes | No |
| V3 | Sodium poly-phosphate A | Amorphous | — | 7 | Yes | No |
| V4 | Sodium poly-phosphate B | Amorphous | — | 15 | Yes | No |
| V5 | Sodium poly-phosphate C | Amorphous | Approx. 27 | 31 | 99% | No |
| V6 | Sodium poly-phosphate D | Amorphous | — | — | 98% | No |
| 1 | Sodium poly-phosphate E | Crystalline | 44 | — | No | Yes |
| 2 | Ammonium poly-phosphate A | Crystalline | 38 | — | No | Yes |
| 3 | Ammonium poly-phosphate B | Crystalline | 110 | — | No | Yes |
| 4 | Calcium poly-phosphate | Crystalline | 16 | — | No | Yes |
| 5 | Potassium poly-phosphate | Crystalline | 31 | — | No | Yes |
| V7 | Sodium trimeta-phosphate | Crystalline | Three-membered ring | — | Yes | No |
| V8 | Calcium hydrogen phosphate | Crystalline | 1 | — | No | No |

The invention claimed is:

1. A method for treating bleeding wounds comprising applying a composition that comprises a polyphosphate in crystalline form, wherein an anion of the polyphosphate has on average (number average) at least 4 phosphorus atoms per polyphosphate anion, and wherein the crystalline polyphosphate is substantially water-insoluble.

2. The method of claim 1, wherein the polyphosphate has a degree of crystallinity, determined by X-ray diffractometry, of at least 90%.

3. The method of claim 2, wherein the anion of the polyphosphate is substantially linear.

4. The method of claim 1, wherein the polyphosphate anion has on average from 8 to 500 phosphorus atoms.

5. The method of claim 1, wherein cations of the polyphosphate are independently selected from $Na^+$, $K^+$, $NH_4^+$, $Ca^{2+}$, $Mg^{2+}$, $Zn^{2+}$, $Sn^{2+}$, $Fe^{3+}$ and $Al^{3+}$.

6. The method of claim 5, wherein the cations of the polyphosphate are selected from $Na^+$, $K^+$, $NH_4^+$ and $Ca^{2+}$.

7. The method of claim 1, wherein particles of the crystalline polyphosphate have a weight-average particle size within the range of 1 μm to 1 mm.

8. The method of claim 2, wherein the degree of crystallinity is at least 95%.

9. The method of claim 1, wherein the polyphosphate anion has an average 12 to 300 phosphorus atoms.

10. The method of claim 1, wherein the polyphosphate anion has an average 15 to 150 phosphorus atoms.

11. The method of claim 7, wherein the particles of the crystalline polyphosphate have a weight-average particle size within the range of 1 mm to 0.5 mm.

12. The method of claim 6, wherein the cations of the polyphosphate are selected from $Na^+$, $K^+$ and $NH_4^+$.

13. The method of claim 1, wherein the polyphosphate has a degree of crystallinity of at least 95% as determined by X-ray diffractometry, wherein the polyphosphate anion has on average from 15 to 150 phosphorus atoms; and wherein the cations of the polyphosphate are selected from $Na^+$, $K^+$, $NH_4^+$ and $Ca^{2+}$.

14. The method of claim 13, wherein the cations of the polyphosphate are selected from $Na^+$, $K^+$ and $NH_4^+$.

\* \* \* \* \*